(12) United States Patent
Morneault

(10) Patent No.: US 9,168,323 B2
(45) Date of Patent: Oct. 27, 2015

(54) HYDROXYL GENERATOR

(71) Applicant: HGI Industries, Inc., Boynton Beach, FL (US)

(72) Inventor: Guy J. E. Morneault, Boynton Beach, FL (US)

(73) Assignee: HGI Industries, Inc., Boynton Beach, FL (US)

( * ) Notice: Subject to any disclaimer, the term of this patent is extended or adjusted under 35 U.S.C. 154(b) by 0 days.

(21) Appl. No.: 14/282,017

(22) Filed: May 20, 2014

(65) Prior Publication Data

US 2014/0314627 A1  Oct. 23, 2014

Related U.S. Application Data

(60) Continuation of application No. 13/600,955, filed on Aug. 31, 2012, now Pat. No. 8,765,072, which is a division of application No. 12/385,981, filed on Apr. 27, 2009, now Pat. No. 8,257,649.

(51) Int. Cl.
*H01T 19/04* (2006.01)
*B01D 53/00* (2006.01)
(Continued)

(52) U.S. Cl.
CPC . *A61L 9/032* (2013.01); *A61L 9/20* (2013.01); *B01D 53/007* (2013.01); *A61L 9/00* (2013.01); *A61L 9/03* (2013.01); *A61L 9/205* (2013.01); *B01D 2257/708* (2013.01);
(Continued)

(58) Field of Classification Search
CPC ............. A61L 9/00; A61L 9/03; A61L 9/032; A61L 9/20; A61L 9/205

USPC ................... 422/186.31, 1, 4–5, 22, 24, 121, 422/123–124, 306, 900, 907; 96/16, 57–58, 96/224; 250/324, 424; 204/157.3; 454/187
See application file for complete search history.

(56) References Cited

U.S. PATENT DOCUMENTS

| 5,236,672 A | 8/1993 | Nunez et al. |
| 5,935,525 A | 8/1999 | Lincoln et al. |

(Continued)

FOREIGN PATENT DOCUMENTS

| EP | 0 461 310 A1 | 12/1991 | ................ A61L 9/20 |
| EP | 0461310 | 12/1991 | |

(Continued)

OTHER PUBLICATIONS

International Search Report and Written Opinion mailed Aug. 27, 2010, PCT/US2010/032476.

(Continued)

*Primary Examiner* — Monzer R Chorbaji
(74) *Attorney, Agent, or Firm* — Fleit Gibbons Gutman Bongini & Bianco PL; Jon A. Gibbons

(57) ABSTRACT

Superior hydroxyls are provided which have effects on organic and inorganic compounds and/or pollutants over substantial periods of time and/or at substantial distances from where the superior hydroxyls are generated. Also provided is a hydroxyl generator, in which UV lamps are positioned such that the coronas which they produce when emitting UV radiation fill substantially all the interior space of the hydroxyl generator. The coronas overlap each other by a maximum amount of between 5% and 25% of the radius of each corona.

33 Claims, 3 Drawing Sheets

(51) Int. Cl.

| | | |
|---|---|---|
| *B03C 3/38* | (2006.01) | |
| *A61L 9/00* | (2006.01) | |
| *B01L 1/04* | (2006.01) | |
| *A61L 9/03* | (2006.01) | |
| *A61L 9/20* | (2006.01) | |
| *H01J 17/00* | (2006.01) | |

(52) U.S. Cl.
CPC .......... *B01D 2259/804* (2013.01); *H01J 17/00* (2013.01); *Y10S 422/90* (2013.01); *Y10S 422/907* (2013.01)

(56) References Cited

U.S. PATENT DOCUMENTS

| | | | | |
|---|---|---|---|---|
| 6,500,387 | B1 * | 12/2002 | Bigelow | 422/24 |
| 6,969,487 | B1 | 11/2005 | Sias et al. | |
| 7,048,776 | B2 * | 5/2006 | Moore et al. | 95/8 |
| 8,765,072 | B2 * | 7/2014 | Morneault | 422/306 |
| 2001/0043887 | A1 | 11/2001 | Morneault et al. | |
| 2002/0094298 | A1 | 7/2002 | Monagan | |
| 2004/0052680 | A1 | 3/2004 | Elwood et al. | 422/24 |
| 2005/0181951 | A1 | 8/2005 | Iwasaki et al. | |
| 2005/0186108 | A1 | 8/2005 | Fields | |
| 2005/0186124 | A1 | 8/2005 | Fink et al. | |
| 2006/0002836 | A1 | 1/2006 | Kim | |
| 2006/0043026 | A1 | 3/2006 | Law et al. | |
| 2007/0217944 | A1 | 9/2007 | Potember et al. | |
| 2008/0056934 | A1 | 3/2008 | Tsui | |
| 2008/0093210 | A1 | 4/2008 | Edwards | |

FOREIGN PATENT DOCUMENTS

| | | | |
|---|---|---|---|
| EP | 1208853 | 5/2002 | |
| EP | 1 977 771 A1 * | 10/2008 | ................ A61L 9/20 |
| EP | 1977771 | 10/2008 | |
| JP | 64-088079 | 4/1989 | |
| JP | 01-234729 | 9/1989 | |
| JP | 05-245191 | 9/1993 | |
| JP | 06-217685 | 8/1994 | |
| JP | 10-057749 | 3/1998 | |
| JP | 11-000390 | 1/1999 | |
| JP | 2001-046906 | 2/2001 | |
| WO | WO 9517634 | 6/1995 | |
| WO | WO 03/061717 | 7/2003 | |
| WO | WO 2007/057520 | 5/2007 | |

OTHER PUBLICATIONS

Kowalski et al., "UVGI Design Basics for Air and Surface Disinfection," HPAC Engineering, Jan. 2000.

* cited by examiner

HYDROXYL GENERATOR

CROSS-REFERENCE TO RELATED APPLICATIONS

This application is a continuation of, and claims priority from, U.S. patent application Ser. No. 13/600,955 filed on Aug. 31, 2012, now U.S. Pat. No. 8,765,072, which is a divisional of, and claims priority from, U.S. patent application Ser. No. 12/385,981 filed on Apr. 27, 2009, now U.S. Pat. No. 8,257,649, the entire disclosure of each is hereby incorporated by reference in its entirety.

BACKGROUND OF THE INVENTION

Hydroxyls are ions of chemical formula O—H which exist in nature and typically are formed by the interaction of ultraviolet (UV) radiation and atmospheric water vapor:

$$H_2O + UV \text{ radiation} \rightarrow H + OH$$

Hydroxyls are very reactive, and therefore are usually short-lived, as they react with compounds around them. This reactivity makes hydroxyls excellent "scavengers" for compounds which act as pollutants, such as bacteria, viruses, mold, radon, odorous compounds, volatile organic compounds (VOCs), poisonous gases, and thousands of other compounds.

In nature, hydroxyls are formed by solar generated UV radiation, and therefore are only formed outdoors. Hydroxyls can also be created indoors by artificially generated UV radiation having wavelengths of 170-270 nm. UV radiation of these wavelengths is also capable of independently decontaminating airstreams of certain particles. Therefore, prior art devices have been constructed which funnel airstreams through banks of UV radiation for the purpose of cleansing the air. Such devices are shown, for example, in U.S. Pat. No. 5,935,525, and U.S. Patent Publication No. 2001/0043887, the disclosures of which are incorporated by reference.

Such devices are taught to be useful for purifying air. However, they suffer from the drawback that they can only purify air which is drawn or blown through the device—that is, in direct proximity to the UV radiation sources—which limits their effectiveness in large indoor settings, such as in a warehouse. Moreover, the need to bring the dirty air in close proximity to the UV radiation source, limits the ability of the devices to disinfect the surfaces of objects located even short distances away from them. For example, prior art devices, if operating in a warehouse suffering from fire damage, would not be able to deodorize cardboard boxes which had absorbed smoke from the fire.

Therefore, there is a need for an improved device which generates hydroxyls which are, and whose effects are, relatively long-lived, and which can be used to purify large volumes of air and objects which come into contact with that air.

OBJECTS OF THE INVENTION

It is therefore, an object of the invention to provide an improved hydroxyl generator.

It is a further object of the invention to provide a method of producing hydroxyls by using the improved hydroxyl generator.

It is still a further object of the invention to provide superior hydroxyls, as hereinafter defined.

It is a further object of the invention to provide superior hydroxyls produced using the improved hydroxyl generator.

It is a further object of the invention to provide a method of disinfecting air by generating hydroxyls using the improved hydroxyl generator and injecting the hydroxyls into the air.

It is a further object of the invention to provide a method of deodorizing air by generating hydroxyls using the improved hydroxyl generator and injecting the hydroxyls into the air.

It is a further object of the invention to provide methods for deodorizing and/or disinfecting objects located outside of the device using the superior hydroxyls of the invention, including the surfaces of such objects and the interior sections of porous objects.

These and other objects of the invention are achieved as outlined in this application.

SUMMARY OF THE INVENTION

This invention provides an improved hydroxyl generator, comprising (A) a housing having an interior surface and an exterior surface, the interior surface defining an interior space having one or more apertures to permit the entrance and exit of air into the interior space; and (B) a plurality of UV lamps, each of which creates a corona when generating UV radiation, the corona having a radius, wherein the coronas from the plurality of lamps fill substantially all the interior space of the housing, and further wherein the coronas of adjacent UV-generating lamps overlap each other by an amount sufficient to generate superior hydroxyls. Preferably, the overlap is a maximum amount of between 5% and 25% of the radius of the corona.

The invention is also directed to a method of producing hydroxyls comprising activating the UV lamps of the hydroxyl generator of the invention to generate UV radiation, and passing air through the interior space of the hydroxyl generator.

The invention is further directed to the superior hydroxyls produced with the hydroxyl generator of the invention. These superior hydroxyls—and their effects—are particularly long-lasting compared to hydroxyls produced using prior art methods, and therefore can be used in different—and more effective—ways.

DETAILED DESCRIPTION OF THE PREFERRED EMBODIMENTS

Figure 1:
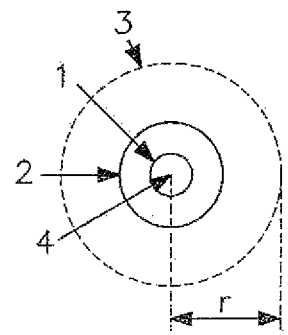
FIG. 1 is a schematic, overhead view of a UV lamp as used in this invention.

The UV radiation used to generate the hydroxyls comes from UV lamps. These UV lamps are available commercially from numerous sources. Preferably, the UV lamps are quartz lamps rather than glass lamps. Preferably, at least some of the UV lamps used in this hydroxyl generator of the invention provide UV radiation having a wavelength of about 185 nm, as this is the most efficient wavelength for generating hydroxyls. UV lamps generating UV radiation having a wavelength of 254 nm are also useful for direct treatment of air inside the hydroxyl generator, but at least some of the UV lamps should generate UV radiation with a wavelength of about 185 nm. It is also preferred that the UV lamps be surrounded by a protective sleeve. The protective sleeve should be transparent to the UV radiation generated by the lamp. A preferred sleeve is made of a material known as double virgin quartz. Protective sleeves are generally available from manufacturers of UV lamps.

In many applications, the UV lamp will have a linear shape but, as will be discussed in more detail below, it can also be bent or curved.

As used in this application, the term "superior hydroxyls" means hydroxyls whose effects persist for a substantial period of time and/or can be observed at a substantial distance from the hydroxyl generator. Prior art hydroxyls were only effective on air which was directly adjacent to the UV lamps. By contrast, the superior hydroxyls of the invention can destroy VOCs at a distance of more than 10 feet away from the generator, preferably more than 30 feet away, and most preferably more than 50 feet away, and for a period of time of at least 1 minute after the generator is turned off, more preferably at least 3 minutes after, more preferably at least 5 minutes after, and most preferably more than 10 minutes.

The superior hydroxyls and/or the effects of the superior hydroxyls of the invention can be transported over substantial distances by moving air, the air being moved by conventional equipment, such as fans and blowers.

The generation of superior hydroxyls can be detected as follows: A fixed amount of volatile organic compounds of known composition is introduced into an enclosed space of fixed volume. The concentration of VOCs in the space is measured immediately and then measured every 2 minutes for a period of twenty minutes. If the enclosed space is very large, the intervals between measurements can be increased, for example to 5 or 10 minutes, as can the total time. The concentration of VOCs is measured using commercially available devices, such as those available from the Dräger Corporation. This procedure establishes a control VOC degradation curve.

A hydroxyl generator is then operated for a period of two minutes, inside the enclosed space used for the control. At the end of that time, the generator is turned off, followed by injection into the space of the same fixed amount of VOCs—and the same composition—as used in the control. The concentration of VOCs in the enclosed volume is then measured immediately, and then re-measured every two minutes for a period of twenty minutes total. If the concentration of VOCs at any of the measuring times is more than 10% below the corresponding control, then it is known that superior hydroxyls were created. It should be noted that use of the hydroxyl generator described as part of this invention will generate VOC concentrations from 15% to 40% or more below the corresponding control.

FIG. 1 shows a schematic, overhead view of a UV lamp and sleeve used in the invention. The outside of the lamp 1 is shown as a circle, with sleeve 2 disposed concentrically around it. If lamp 1 is activated and is generating UV radiation, it will also generate a "corona." As used in this application, "corona," or NIR region means the halo which may be observed around a UV lamp when the lamp is operating and generating UV radiation and photographed with any commercially available infra-red camera, which measures radiation in the near-infrared region of 700-900 nm. The nature of this corona is not precisely understood, but it is plainly visible using the methods described herein. Without wishing to be bound by theory, it is believed the corona results from photo-energy given off by reactions taking place due to the interaction of the UV radiation with the molecules in the airstream passing by the UV lamps.

Figure 2:
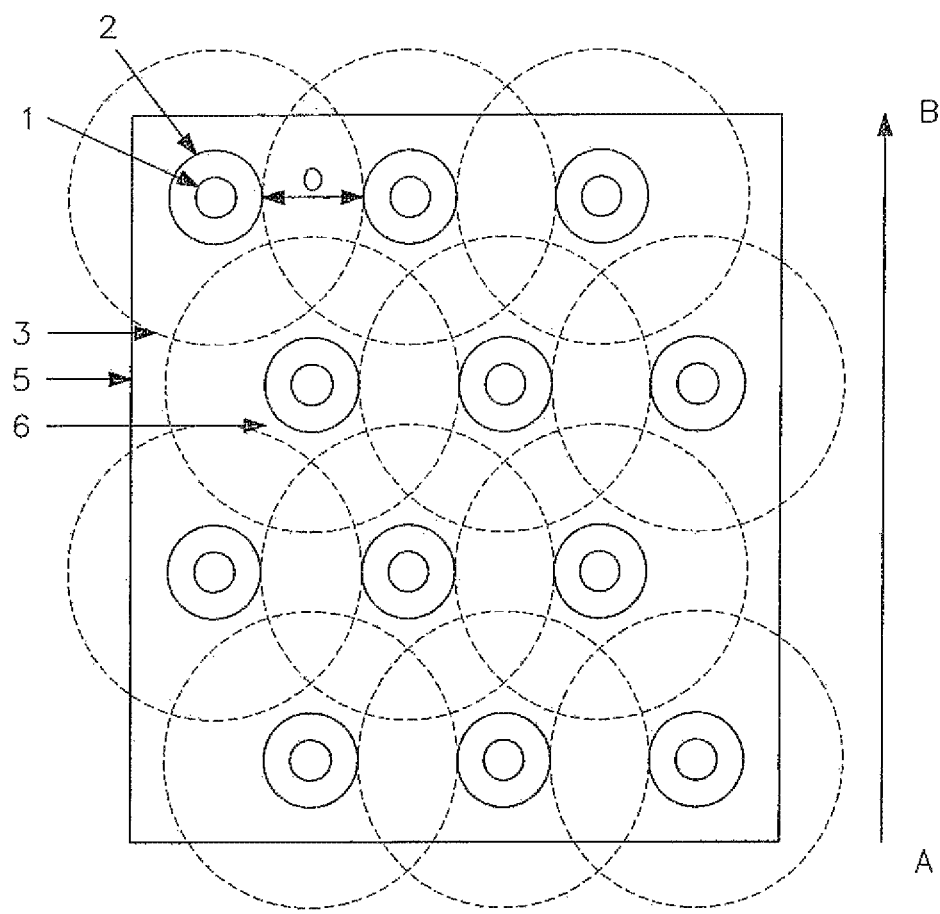
FIG. 2 is a schematic, overhead view of the arrangement of the UV lamps in the hydroxyl generator of the invention.

The outer edges of the corona are shown in FIGS. 1 and 2 by broken circle 3. Corona 3 has a radius r which may be measured from the center 4 of lamp 1 to the edge of corona 3.

In practice, a person of skill in the art will be able to determine the radius of the corona for a given lamp by taking infra-red photographs of a number of different samples of the lamp. Using these photographs, the size of the corona—in particular its radius, as measured from the center of the UV lamp—can be measured and averaged over the entire line of lamps.

Using this information, a plurality of lamps is arranged inside a housing so that the coronas of the UV lamps overlap. The housing has an exterior surface and an interior surface. The interior surface of the housing defines an interior space. When the UV lamps are operating, the coronas from the UV lamps fill substantially all the volume of the interior space. By "substantially all", what is meant is at least 75%, preferably 85%, more preferably 95%, more preferably 97%, and most preferably 99%, of the total volume of the interior space. In some preferred embodiments, 100% of the volume of the interior space is filled with coronas from the UV lamps.

Alternatively, a single UV lamp can be used inside the housing, either a straight, curved, or bent lamp, which is positioned inside a housing so that its corona fills substantially all the interior space of that housing.

The UV lamps are positioned such that when air is passed through the generator in which the UV lamps are operating, superior hydroxyls are generated. Preferably, the lamps are positioned such that their respective coronas only overlap each other by an amount which as its maximum is between 5% and 25% of the radius of the corona. An example of this arrangement is shown in FIG. 2, which is a schematic, overhead view of the arrangement of the UV lamps in the hydroxyl generator of the invention. In FIG. 2, a plurality of UV lamps 1 are shown, each surrounded by a sleeve 2, and producing a corona 3. The UV lamps are located within housing 5, which defines an interior space 6. The coronas 3 of the lamps 1 substantially fill all the interior space 6. The housing is designed so that air can pass through the housing, for example in the direction indicated by the arrow marked A B.

Figure 3:
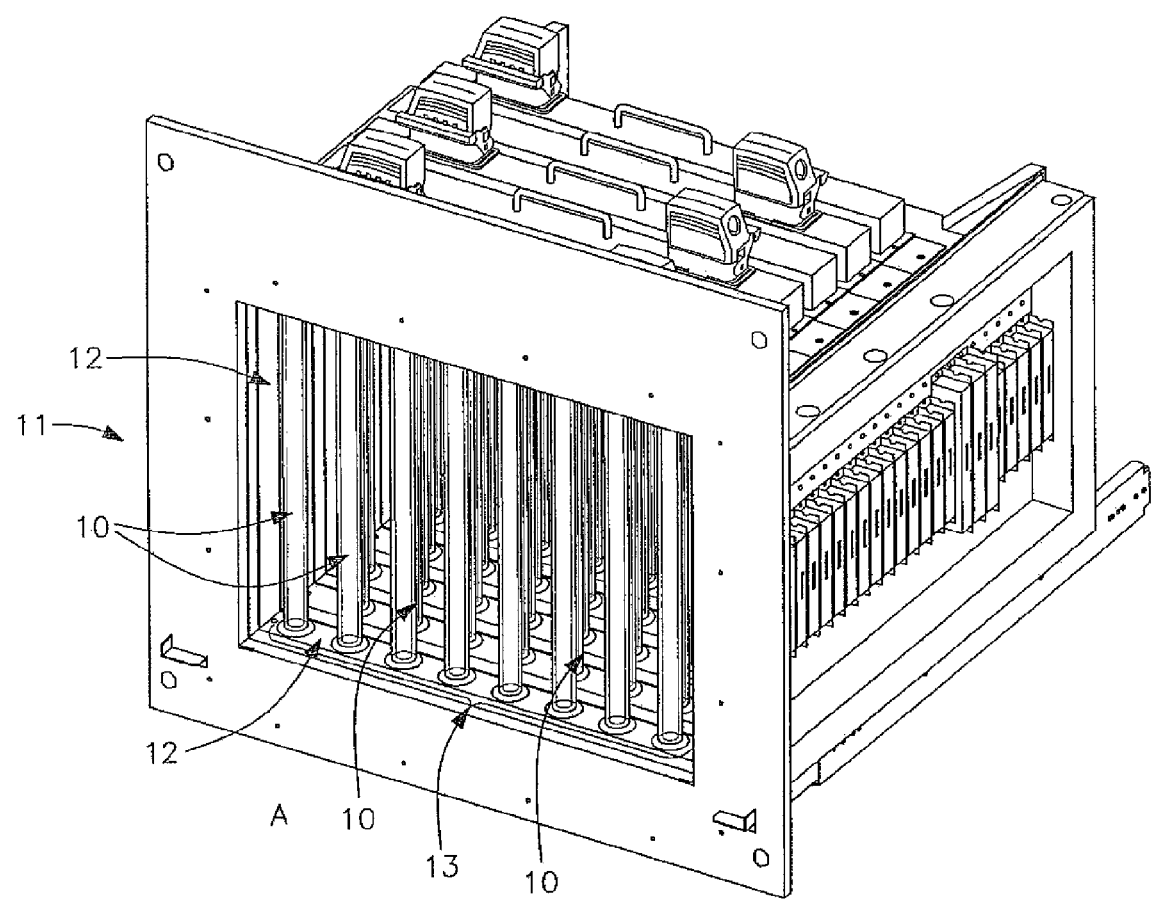
FIG. 3 is a perspective, cut away view of a hydroxyl generator according to the invention.

A perspective view of a hydroxyl generator according to the invention is shown in FIG. 3. UV lamp/protective sleeve combinations 10 are arranged inside a housing 11. Air is directed into the interior of the housing through side A by any conventional air moving means (not shown) when the UV lamps are activated. Preferably, at least the first row 13 of UV lamps generates UV radiation having a wavelength of 185 nm. This provides for the generation of large amounts of hydroxyls, which are carried in the airstream towards side B of the generator. Without wishing to be bound by theory, it is believed that as the hydroxyls pass through the hydroxyl generator from side A to side B, they gain more and more energy; when the hydroxyls exit the generator at side B, they have become "superior hydroxyls".

It has been found that increasing the number of lamps in a single generator geometrically increases the effectiveness of the hydroxyls created by the hydroxyl generator. That is, an 8-lamp generator will be, all things being otherwise equal, more than twice as effective as a 4-lamp generator.

Air can be fed through the hydroxyl generator by conventional air moving devices (not shown in the drawings), such as, for example, but not limited to, fans, pumps, blowers, etc. Baffles and other physical structures may also be used to regulate how long it takes air to pass through the housing.

Preferably, air will be present inside the housing for a period of at least 170 milliseconds, more preferably at least 250 milliseconds, and most preferably at least 340 milliseconds.

In a preferred embodiment, each UV lamp is cylindrical and has an exterior diameter of ¾ of an inch, and is surrounded by a cylindrical sleeve with an interior diameter of 1 inch and an exterior diameter of 1⅛ inches. In the preferred embodiment, the UV lamp produces a corona with a diameter of 3¾ inches, and the lamps are positioned such that their centers are 3 inches apart, and 1½ inches from the inside surface of the housing. Preferably, the UV lamps are positioned in rows, with each row being slightly offset from the immediately adjacent rows, as may be seen in FIG. 3.

Figure 4:
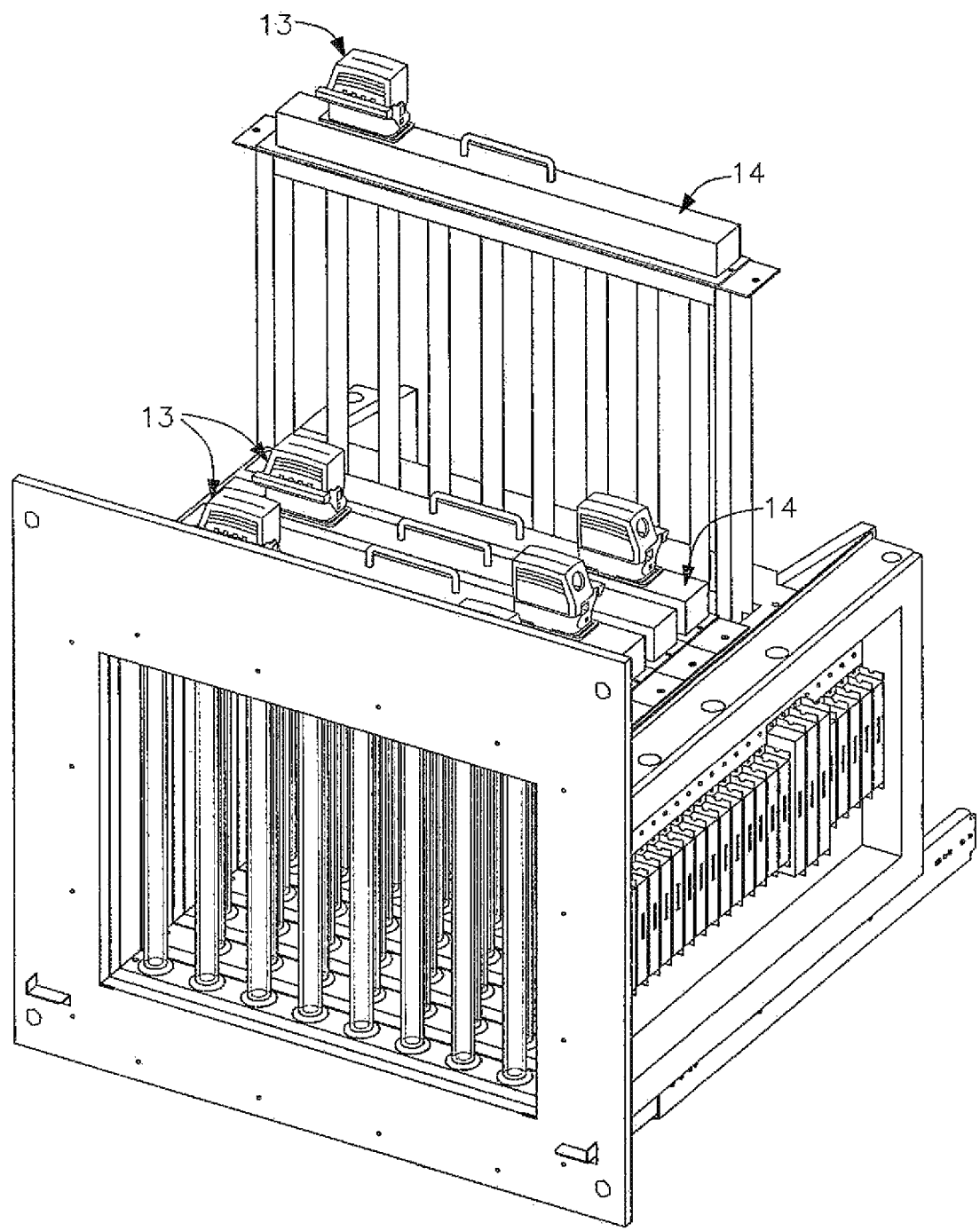
FIG. 4 is a perspective, cut away view of a hydroxyl generator according to the invention showing a rack of UV lamps partially removed from the device.

The housing need not be made of a single piece of material, but may be composed of two or more pieces which fit closely together so as to define an interior space. An example of this type of design is shown in FIG. 3. Rows 13 of UV lamps may be located on removable racks 14, as shown in FIG. 4. When the removable racks are lowered into position, they serve to define the housing.

Preferably, the interior surface of the housing is reflective of UV radiation. In one preferred embodiment, the interior surface of the housing is made of aluminum, more preferably unpolished aluminum.

The hydroxyl generator may optionally include a means for imparting humidity in the air. The means for imparting humidity can be integral to the housing, or it can be detachably attached to the housing. The means for imparting humidity is used when the ambient humidity is extremely low, such that there is essentially no water vapor in the air. Preferably, the means for imparting humidity is used when the ambient relative humidity is lower than 5%, more preferably when the ambient humidity is lower than 10%, and most preferably when the ambient humidity is lower than 15%. When the ambient humidity is higher than 15%, it is generally not necessary to use the means for imparting humidity. The means for imparting humidity is conventional, and is known as a water curtain.

Another aspect of the present invention is a process for creating hydroxyls with the improved hydroxyl generator described above. In this method, the UV lamps of the hydroxyl generator of the invention are activated to generate UV radiation, and moist air is passed through the interior space of the hydroxyl generator. By "moist air," we mean air with sufficient water vapor to form hydroxyls. Preferably, moist air has at least 5% ambient humidity, more preferably 10% ambient humidity, and most preferably at least 15% humidity. If necessary, the ambient air which is passed through the generator is humidified using a means for imparting humidity. Preferably, the air is resident in the interior space of the generator for at least 170 milliseconds.

The invention also comprises a method of disinfecting and/or deodorizing air, which comprises the steps of generating hydroxyls using the hydroxyl generator of the invention and then distributing the hydroxyls over the space to be disinfected and/or deodorized using air moving equipment, such as fans or blowers. For example, the air around smelly commercial facilities, such as pig farms, and rendering plants can be deodorized using the hydroxyl generators according to the invention so that air exiting from the facility is less odorous or even odor-free.

Another use of the hydroxyl generator according to the invention is in the deodorizing of indoor air spaces following fires, floods, or other odor-generating activities. A further use of the hydroxyl generator according to the invention is the decontamination and/or remediation of biological pathogens, including biological weapons, such as anthrax.

The hydroxyls created using the hydroxyl generator of this invention are superior hydroxyls, as defined above, and were not known prior to this invention. The superior hydroxyls—and their deodorizing/disinfecting effects—are sufficiently long-lived that they can act as deodorizers and disinfectants at distances of hundreds of feet, or even farther, from the generator.

In another example, following a fire in a consumer warehouse-style retail store, the entire store, and all the cardboard boxes in the store containing otherwise undamaged merchandise smelled very badly of smoke. Hydroxyl generators according to the invention were operating inside the store for a period of four days. At the end of that time, not only was the smoky smell completely gone from the air, all the merchandise, some of which was located hundreds of feet from the generator, was also smoke free. This could only have happened if the hydroxyls created in the generator and/or their effects were very long lived and were capable of being transported by moving air, giving them an opportunity to be circulated throughout the store and allowed to penetrate into the merchandise.

I claim:

1. A hydroxyl generator comprising:
a housing having an interior surface and an exterior surface, the interior surface defining an interior space having one or more apertures to permit entrance and exit of air into and out of the interior space, the housing having baffles for regulating how long it takes for air to pass through the housing;
a blower or fan for moving air from outside the housing into the interior space and for ejecting air from the interior space; and
ultraviolet (UV) lamps arranged within the interior space, each of which, when generating UV radiation, creates in proximity to a surface of the UV lamp a near-infrared (NIR) region, wherein the NIR regions of adjacent UV lamps overlap each other by less than 25% of the radius of the NIR regions,
wherein the NIR regions from the UV lamps fill substantially all the interior space of the housing, whereby substantially all air entering the housing can only leave after having passed through at least one NIR region and is ejected from the interior space while containing hydroxyl radicals.

2. The hydroxyl generator of claim 1, wherein the UV lamps are arranged in one or more rows.

3. The hydroxyl generator of claim 2, wherein the UV lamps are arranged in more than one row, and wherein the rows are arranged in an offset manner.

4. The hydroxyl generator of claim 3, wherein each row of the one or more of the rows of UV lamps is independently removable from the housing.

5. The hydroxyl generator of claim 4, wherein the interior surface comprises aluminum.

6. The hydroxyl generator of claim 2, wherein the one or more of the rows of UV lamps is removable from the housing.

7. The hydroxyl generator of claim 6, wherein the interior surface reflects the UV radiation generated by the UV lamps.

8. The hydroxyl generator of claim 3, wherein the interior surface reflects the UV radiation generated by the UV lamps.

9. The hydroxyl generator of claim 2, wherein the interior surface reflects the UV radiation generated by the UV lamps.

10. The hydroxyl generator of claim 1, wherein the interior surface reflects the UV radiation generated by the UV lamps.

11. The hydroxyl generator of claim 1, further comprising:
a humidifier to produce moist air, with at least 5% ambient humidity, through the interior space of the housing.

12. The hydroxyl generator of claim 1, wherein the baffles cause the moving air to be present inside the housing for at least 340 milliseconds.

13. The hydroxyl generator of claim 1, wherein each of the one or more UV lamps generates UV radiation with a wavelength of about 185 nm.

14. A hydroxyl generator comprising:
   a housing having an interior surface and an exterior surface, the interior surface defining an interior space having one or more apertures to permit entrance and exit of air into and out of the interior space;
   a blower or fan for moving air from outside the housing into the interior space and for ejecting air from the interior space; and
   ultraviolet (UV) lamps, each UV lamp being cylindrical and having an exterior diameter of ¾ of an inch, arranged within the interior space such that centers of the UV lamps are 3 inches apart, each of which, when generating UV radiation, creates in proximity to a surface of the UV lamp one or more near-infrared (NIR) regions having a diameter of 3¾ inches, wherein the NIR regions of adjacent UV lamps overlap each other by an amount of less than 25% of the radius of the NIR region,
   wherein the NIR regions from the UV lamps fill substantially all the interior space of the housing, whereby substantially all air entering the housing can only leave after having passed through at least one NIR region and is ejected from the interior space while containing hydroxyl radicals.

15. The hydroxyl generator of claim 14, wherein at least one of the UV lamps generates UV radiation with a wavelength of about 185 nm.

16. The hydroxyl generator of claim 14, wherein the UV lamps are arranged in two or more rows.

17. The hydroxyl generator of claim 16, wherein the two or more rows are arranged in an offset manner.

18. The hydroxyl generator of claim 16, wherein the two or more of the rows of UV lamps are removable from the housing.

19. The hydroxyl generator of claim 16, wherein each row of the two or more rows of UV lamps is independently removable from the housing.

20. The hydroxyl generator of claim 14, wherein the interior surface is 1½ inches from a centerline of UV lamps nearest the interior surface, and wherein the interior surface reflects the UV radiation generated by the UV lamps.

21. The hydroxyl generator of claim 14, further comprising:
   a means for adding humidity to produce moist air, with at least 5% ambient humidity, through the interior space of the housing.

22. A hydroxyl generator comprising:
   a housing having an interior surface and an exterior surface, the interior surface defining an interior space having one or more apertures to permit entrance and exit of air into and out of the interior space, the housing having baffles for regulating how long it takes for air to pass through the housing;
   an air moving device for moving air from outside the housing into the interior space and for ejecting air from the interior space, wherein the moving air is present inside the housing for at least 170 milliseconds; and
   ultraviolet (UV) lamps, each of which, when generating UV radiation, creates in proximity to a surface of the UV lamp a near-infrared (NIR) region,
   wherein the NIR regions fill substantially all the interior space of the housing whereby substantially all air entering the housing can only leave after having passed through at least one NIR region and is ejected from the interior space while containing superior hydroxyl radicals, and
   wherein the NIR regions of adjacent UV lamps overlap each other by a distance of less than 25% of the radius of the NIR region.

23. The hydroxyl generator of claim 22, wherein each UV lamp is cylindrical and has an exterior diameter of ¾ of an inch, and wherein the UV lamps are arranged within the interior space such that centers of the UV lamps are 3 inches apart.

24. The hydroxyl generator of claim 23, wherein each NIR region has a diameter of 3¾ inches.

25. The hydroxyl generator of claim 23, wherein each UV lamp generates UV radiation with a wavelength of less than 240 nm.

26. The hydroxyl generator of claim 22, wherein the interior surface is 1½ inches from a centerline of UV lamps nearest the interior surface, and wherein the interior surface reflects the UV radiation generated by the UV lamps.

27. The hydroxyl generator of claim 22, wherein the UV lamps are arranged in a single row.

28. The hydroxyl generator of claim 22, wherein the UV lamps are arranged in two or more rows.

29. The hydroxyl generator of claim 28, wherein the two or more rows are arranged in an offset manner.

30. The hydroxyl generator of claim 28, wherein the two or more of the rows of UV lamps are removable from the housing.

31. The hydroxyl generator of claim 28, wherein each row of the two or more rows of UV lamps is independently removable from the housing.

32. The hydroxyl generator of claim 22, wherein the interior surface is 1½ inches from a centerline of UV lamps nearest the interior surface, and wherein the interior surface reflects the UV radiation generated by the UV lamps.

33. The hydroxyl generator of claim 22, further comprising:
   means for adding humidity to produce moist air, with at least 5% ambient humidity, through the interior space of the housing.

* * * * *